United States Patent
Uchiyama et al.

(10) Patent No.: US 6,471,944 B1
(45) Date of Patent: Oct. 29, 2002

(54) AEROSOL POWDER WITH IMPROVED SKIN ADHESION

(75) Inventors: Tsuyoshi Uchiyama, Tokyo (JP); Megumi Suzuki, Tokyo (JP); Ariko Imaoji, Tokyo (JP)

(73) Assignee: Taisho Pharmaceutical Co., Ltd. (JP)

( * ) Notice: Subject to any disclaimer, the term of this patent is extended or adjusted under 35 U.S.C. 154(b) by 0 days.

(21) Appl. No.: 09/463,500

(22) PCT Filed: Aug. 5, 1998

(86) PCT No.: PCT/JP98/03489

§ 371 (c)(1),
(2), (4) Date: Jan. 27, 2000

(87) PCT Pub. No.: WO99/07344

PCT Pub. Date: Feb. 18, 1999

(30) Foreign Application Priority Data

Aug. 7, 1997 (JP) .............................. 9-212356

(51) Int. Cl.[7] .............................. A61L 9/04; A61K 9/14; A61K 9/00; A61K 31/74
(52) U.S. Cl. .............................. 424/45; 424/46; 424/47; 424/78.02; 424/78.03; 424/489
(58) Field of Search .............................. 424/45, 46, 47, 424/78.02, 78.03, 489

(56) References Cited

U.S. PATENT DOCUMENTS

| | | | | |
|---|---|---|---|---|
| 4,174,295 A | * | 11/1979 | Bargigia et al. | |
| 4,595,522 A | * | 6/1986 | Bartlett et al. | |
| 5,209,921 A | | 5/1993 | Brobyn et al. | |
| 5,397,564 A | * | 3/1995 | Seki et al. | |
| 5,976,504 A | * | 11/1999 | Russell | |

FOREIGN PATENT DOCUMENTS

| | | |
|---|---|---|
| JP | 60-215092 | 10/1985 |
| JP | 3-11012 | 1/1991 |
| JP | 3-118313 | 5/1991 |
| JP | 3-209315 | 9/1991 |
| JP | 6-86815 | 3/1994 |
| JP | 7-25725 | 1/1995 |

* cited by examiner

Primary Examiner—Jose' G. Dees
Assistant Examiner—Robert M. Dewitty
(74) Attorney, Agent, or Firm—Lorusso & Loud

(57) ABSTRACT

Powdery aerosol preparations, which are characterized in that 50 to 90% by weight of a propellant having a vapor pressure at 20° C. of 4.5 kg/cm² or less, 5 to 30% by weight of an aliphatic hydrocarbon having a boiling point of 5 to 40° C., 0.5 to 20% by weight of a powdery component and 1 to 20% by weight of a lower alcohol are packed in a container provided with a straight nozzle button having an orifice of 0.7 to 2.0 mm, show improved adhesion of the powders and the active ingredients to the skin and give an excellent feel in using, are provided.

2 Claims, No Drawings

AEROSOL POWDER WITH IMPROVED SKIN ADHESION

TECHNICAL FIELD

This invention relates to aerosol preparations. More particularly, it relates to powdery aerosol preparations showing improved adhesion of powders and active ingredients on the skin and giving an excellent feel in using.

BACKGROUND ART

Aerosol preparations containing powdery components have been developed to improve the feel in using aerosol products applied onto the surface of the skin and to dry the affected parts or wounds in a moisten state. In these powdery aerosol preparations, various flons were employed as propellants. Since it turned out that flons would cause the environmental disruption, combustible liquefied gases such as liquefied petroleum gas and dimethyl ether have been used as propellants substituting for flons.

However, combustible liquefied gases generally have low boiling points, which brings about some troubles, for example, taking on the latent evaporation heat and thus giving pain on the skin. To avoid the above-described problems, therefore, attempts have been made to spray a powdery aerosol preparation in the form of a fine mist by stopping down the orifice of a valve or a button. In such a case, however, the powder and active ingredient thus sprayed spatter into the atmosphere and, therefore, can be hardly adhered to the skin. Moreover, there arises a fear in safety such as inhalation in using.

Examples of known techniques for enhancing the adhesion of powdery aerosol preparations with the use of these combustible liquefied gases to the skin involve those disclosed in JP-A-60-215092, JP-A-3-118313, JP-A-3-70788, JP-A-3-95289, etc. (the term "JP-A" as used herein means an "unexamined published Japanese patent application"). However, satisfactory adhesion of drugs to the skin cannot be always achieved by these techniques.

DISCLOSURE OF THE INVENTION

As a result of extensive investigation to solve the above-described problems, the present inventors have found out that a very high adhesion rate of a powder and an active ingredient can be obtained by using a combination of a propellant having a low vapor pressure with a straight nozzle button having a large orifice, and that a powdery aerosol preparation, which gives no pain when a low-boiling propellant, etc. is sprayed directly onto the skin and can be dried quickly, can be obtained by using a combination of an aliphatic hydrocarbon having a boiling point of 5 to 40° C. with a lower alcohol. The invention has been completed based on these findings.

Accordingly, the invention provides a powdery aerosol preparation wherein 50 to 90% by weight of a propellant having a vapor pressure at 20° C. of 4.5 kg/cm$^2$ or less, 5 to 30% by weight of an aliphatic hydrocarbon having a boiling point of 5 to 40° C., 0.5 to 20% by weight of a powdery component and 1 to 20% by weight of a lower alcohol are packed in a container provided with a straight nozzle button having an orifice of 0.7 to 2.0 mm.

The propellant to be used in the invention is one which is selected from propane, n-butane, isobutane and dimethyl ether or a mixture of two or more thereof and has a vapor pressure at 20° C. of 4.5 kg/cm$^2$ or less. When it is a mixture having a vapor pressure exceeding 4.5 kg/cm$^2$, the ratio of propane (boiling point: −40° C.) or dimethyl ether (boiling point: −24° C.) becomes larger and the propellant vaporizes before it reaches the skin. As a result, the powder is atomized and spatters, thereby lowering the adhesion rate to the skin and causing a risk of inhalation.

Examples of the aliphatic hydrocarbon having a boiling point of 5 to 40° C. include n-pentane (boiling point: 36.1° C.), isopentane (boiling point: 27.9° C.) and neopentane (boiling point: 9.5° C.). By using such an aliphatic hydrocarbon, the boiling point of the whole composition can be elevated to a certain level. Thus, the immediate vaporization of the propellant can be prevented and the spattering caused by the atomization of the powder can be regulated. At the same time, the pain on the skin at the spraying can be avoided thereby. It is preferable that the content of the aliphatic hydrocarbon ranges from 5 to 30% by weight of the whole aerosol composition. When the content thereof is smaller than 5% by weight, the above-described effects cannot be fully expressed. On the other hand, it is unfavorable that the content thereof exceeds 30% by weight, since the spray power is weakened due to a decrease in the inner pressure of the aerosol preparation thereby causing clogging with the powder. In this case, there arise additional unfavorable phenomena such as excessively broadened spray pattern and dripping.

The content of the combustible liquefied gas serving as the propellant preferably ranges from 50 to 90% by weight based on the whole aerosol composition. It is unfavorable that the content thereof is smaller than 50% by weight, since the spray power is weakened and thus clogging with the powder occurs in this case. On the other hand, it is also unfavorable that the content thereof exceeds 90%, since the excessively high spray power causes a pain or spattering of the powder.

In the invention, use is further made of a straight nozzle button having an orifice of 0.7 to 2.0 mm. When the orifice is less than 0.7 mm, no favorable preparation can be obtained. This is because the sprayed matter is atomized to thereby extremely lower the adhesion rate to the skin and the powder spatters largely in this case. It is also unfavorable that the orifice exceeds 2.0 mm, since dripping arises in this case.

The valve is not particularly limited, so long as it is a valve commonly employed for powders. The size of the vapor tap orifice scarcely affects the adhesion rate.

In the invention, the powder component is used in order to give an excellent feel in using by elevating the adhesion of the active ingredient to the skin, enhancing the dryness of a moisten part and improving the slipperiness, lubricating action, etc. and, moreover, it is used for facilitating the production of the powdery aerosol preparation. Examples of the powdery component include inorganic powders (silicic anhydride, magnesium silicate, talc, kaolin, mica, zinc oxide, titanium oxide, magnesium oxide, magnesium carbonate, calamine, magnesium aluminate metasilicate, etc.) and organic powders (corn starch, potato starch, nylon powder, polyethylene powder, polystyrene powder, cellulose powder, etc.). Either one of these powders or a mixture of two or more thereof may be employed.

The content of the powdery component ranges from 0.5 to 20% by weight, preferably from 1 to 15% by weight, based on the whole aerosol composition. When its content is smaller than 0.5% by weight, the above-described objects can be hardly achieved. On the other hand, it is unfavorable that the content thereof exceeds 20% by weight, since there arises clogging with the powder in this case.

In the invention, a lower alcohol (ethyl alcohol, isopropyl alcohol, etc.) is used in an amount of from 1 to 20% by weight, preferably from 3 to 15% by weight, based on the whole aerosol composition in order to promote the dissolution of the active ingredient, improve the dispersion stability of the powder in the aerosol composition, improve the spredability of the sprayed powder and active ingredient, etc. When its content is smaller than 1% by weight, the above-described objects can be hardly achieved. On the other hand, it is unfavorable that the content thereof exceeds 20% by weight, since the sprayed matter cannot be quickly dried but becomes sticky in this case.

The powdery aerosol preparation of the invention may further contain, if required, publicly known additives such as silicone oils (methylpolysiloxane, etc.), hydrocarbons (liquid paraffin, suqalane, etc.), higher fatty acid esters (isopropyl myristate, butyl stearate, etc.), vegetable oils (olive oil, castor oil, etc.), animal oils (beeswax, squalene, etc.), nonionic surfactants (sorbitan sesquioleate, polyglycerol fatty acid esters, etc.) and the like.

The active ingredient to be used in the invention is one expected as achieving a therapeutic effect when applied by spraying. Examples thereof include antifungal agents (miconazole nitrate, clotrimazole, undecylenic acid, tolnaftate, etc.), antisudorific agents (aluminum chlorohydrate), anti-inflammatory and analgesic agents (indomethacin, methyl salicylate, ketoprofen, etc.), antipruritic agents (ichthammol, crotamiton, isothipendyl hydrochloride, chlorpheniramine maleate, etc.), bactericides (potassium iodide, acrinol, benzalkonium chloride, chlorpheniramine gluconate, etc.), drugs against purulent diseases (tetracycline hydrochloride, kanamycin, etc.), topical anesthetics (lidocaine, dibucain hydrochloride, etc.), refrigerants (l-menthol, dl-camphor, etc.), etc.

BEST MODE FOR CARRYING OUT THE INVENTION

The invention will be described in greater detail by reference to the following Examples, but it should be understood that the invention is not construed as being limited thereto. The powdery aerosol preparations prepared herein were evaluated by the following methods.

(1) Method for Evaluating Adhesion Rate

The amount of the drug (miconazole nitrate) per unit weight of the sprayed matters was measured for each of the samples. The sample was sprayed for 1 second onto a glass plate (diameter: 6.5 cm) at a distance 10 cm apart. Then the drug adhered to the glass plate was quantitated and the adhesion rate was calculated in accordance with the following formula. The quantification was repeated thrice and the average was determined. A sample showing an adhesion rate of 60% or above was regarded as "good". Adhesion rate (%)=(weight of drug adhered to glass plate/weight of sprayed matter×weight of drug per unit weight of sprayed matter)×100.

(2) Method for Evaluating Spattering Powder

Samples were each sprayed for 1 second onto a black drawing paper sheet at a distance 10 cm apart. Then the spray patterns of the powders adhering to the paper were compared with each other to thereby evaluate the diffusion of each spray.

⊚: Very little spattering of powder and very little diffusion of spray.

◯: Little spattering of powder and little diffusion of spray.

X: Much spattering of powder and much diffusion of spray.

(3) Method for Evaluating Excessive Cold Feel and Pain

The samples were each sprayed to the forearms of 3 subjects at a distance 10 cm apart and thus evaluated in accordance with the following criteria.

⊚: Giving a refreshing feel but no pain.

◯: Giving neither any refreshing feel nor pain.

X: Giving an excessive cold feel with a pain.

XX: Giving an excessive cold feel and causing erythema on the skin.

(4) Measurement of Skin Surface Temperature by Thermography

The samples were each sprayed for 1 second onto, the forearms of the subjects at a distance 10 cm or 5 cm apart. Immediately after the spraying, the sprayed matter on the skin was wiped off with a paper towel. One second after the completion of the spraying, the skin surface temperature of each subject was measured with a thermograph. The average of 3 subjects was calculated.

EXAMPLES 1 TO 4 AND COMPARATIVE EXAMPLE 1

Aerosol preparations of the following compositions were prepared and the properties were evaluated. Table 1 summarizes the results.

|  | % by weight |
| --- | --- |
| miconazole nitrate | 0.15 |
| lidocaine | 0.3 |
| zinc oxide | 1.4 |
| silicic anhydride | 0.15 |
| talc | 3.0 |
| dimethylpolysiloxane | 0.3 |
| sorbitan monostearate | 0.3 |
| isopropyl myristate | 0.3 |
| ethanol | 9.1 |
| isopentane | 25.0 |
| LPG (20° C., 3 kg/cm$^2$) | 60.0 |

TABLE 1

|  | Ex. 1 | Ex. 2 | Ex. 3 | Ex. 4 | C. Ex. 1 |
| --- | --- | --- | --- | --- | --- |
| Valve* | a | a | a | b | a |
| Button orifice (mm) | 1.02 | 0.86 | 0.76 | 1.02 | 0.51 |
| Adhesion ratio (%) | 74 | 65 | 61 | 71 | 31 |
| Spattering of powder | ⊚ | ⊚ | ◯ | ⊚ | x |
| Excessive cold feel/pain | ⊚ | ⊚ | ⊚ | ◯ | ◯ |

*Specifications of valve:
a: stem orifice 0.51 mm × 2, housing orifice 1.58 mm and vapor tap orifice 0.76 mm.
b: stem orifice 0.51 mm × 2, housing orifice 1.58 mm and vapor tap orifice 1.02 mm.

As shown in Table 1, high adhesion ratios were established and the samples little spattered or scattered in Examples 1 to 4 wherein the orifices of the buttons exceeded 0.7 mm. These samples gave neither excessive cold feel nor pain, thus showing favorable results. In Comparative Example 1, the adhesion ratio was low and the powder largely scattered. In Example 4, the procedure of Example 1 was followed but using a different valve.

EXAMPLES 5 TO 7 AND COMPARATIVE EXAMPLES 2 TO 5

Aerosol preparations having the following compositions and the propellants as listed in Table 2 were prepared and the properties were evaluated.

|  | % by weight |
| --- | --- |
| miconazole nitrate | 0.15 |
| lidocaine | 0.3 |
| zinc oxide | 1.4 |
| silicic anhydride | 0.15 |
| talc | 3.0 |
| dimethylpolysiloxane | 0.3 |
| sorbitan monostearate | 0.3 |
| isopropyl myristate | 0.3 |
| ethanol | 9.1 |

TABLE 2

|  | Ex. 5 | Ex. 6 | Ex. 7 | C. Ex. 2 | C. Ex. 3 | C. Ex. 4 | C. Ex. 5 |
| --- | --- | --- | --- | --- | --- | --- | --- |
| Isopentane | 15.0 | 8.0 | 25.0 | 3.0 | — | — | 25.0 |
| LPG 3.0 | 70.0 | 77.0 | — | 82.0 | 85.0 | 85.0 | — |
| LPG 4.0 | — | — | 60.0 | — | — | — | — |
| LPG 5.0 | — | — | — | — | — | — | 60.0 |
| total | 85.0 | 85.0 | 85.0 | 85.0 | 85.0 | 85.0 | 85.0 |
| Button orifice (mm) | 0.65 | 1.02 | 1.02 | 1.02 | 1.02 | 0.65 | 0.65 |
| Adhesion ratio (%) | 72 | 71 | 62 | 69 | 67 | 42 | 48 |
| Spattering of powder | ⊚ | ⊚ | ○ | ⊚ | ⊚ | X | X |
| Cold feel/pain (10 cm) | ⊚ | ⊚ | ⊚ | X | XX | ○ | ○ |
| Cold feel/pain (5 cm) | — | ⊚ | — | — | XX | XX | — |
| Surface temp. (° C., 10 cm) | — | 18.2 | — | — | 14.3 | 22.1 | — |
| Surface temp. (° C., 5 cm) | — | 16.9 | — | — | 13.2 | 14.9 | — |

Specifications of valve: stem orifice 0.51 mm×2, housing orifice 1.58 mm and vapor tap orifice 0.76 mm. Propellant: LPG 3.0 means LPG having a vapor pressure at 20° C. of 3.0 kg/cm², the same applies to LPG 4.0 and LPG 5.0.

As shown in Table 2, high adhesion ratios were established and the powders little spattered in Examples 5 and 6 and Comparative Examples 2 and 3. The samples of Examples 5 and 6 containing respectively 15% by weight and 8% by weight of isopentane gave no excessive cold feel or pain. In contrast, the samples of Comparative Examples 2 and 3 containing respectively 3% by weight and 0% by weight of isopentane gave each an excessive cold feel and a pain. In Comparative Example 4 wherein no isopentane was employed but the button had an orifice of 0.65 mm, the sprayed matter was atomized. As a result, the powder largely spattered and only a low adhesion ratio was established in this case, though no pain on the skin was noticeable. In Comparative Example 5, the high vapor pressure of the liquefied petroleum gas caused the atomization of the sprayed matter. In this case, therefore, the adhesion ratio was lowered and the powder largely spattered.

The sample of Example 6 gave no pain when sprayed at a distance 10 cm apart as in usual cases. Moreover, it gave no pain even though it was sprayed at a distance 5 cm apart by error, which proves that the preparation has a high safety.

EXAMPLES 8 AND 9 AND COMPARATIVE EXAMPLES 6 AND 7

Aerosol preparations having the following compositions as listed in Table 3 were prepared and the properties were evaluated.

TABLE 3

|  | Ex. 8 | Ex. 9 | C. Ex. 6 | C. Ex. 7 |
| --- | --- | --- | --- | --- |
| Miconazole nitrate | 0.15 | 0.15 | 0.15 | 0.15 |
| Lidocaine | 0.3 | 0.3 | 0.3 | 0.3 |
| Zinc oxide | 1.4 | 1.4 | 1.4 | 1.4 |
| Silicic anhydride | 0.15 | 0.15 | 0.15 | 0.15 |
| Talc | 5.5 | 8.0 | 5.5 | 8.0 |
| Dimethylpolysiloxane | 0.3 | 0.3 | 0.3 | 0.3 |
| Sorbitan monostearate | 0.3 | 0.3 | 0.3 | 0.3 |
| Isopropyl myristate | 0.3 | 0.3 | 0.3 | 0.3 |
| Ethanol | 6.6 | 4.1 | 6.6 | 4.1 |
| Isopentane | 25.0 | 25.0 | — | — |
| LPG. 3.0 | 60.0 | 60.0 | 85.0 | 85.0 |
| total | 100.0 | 100.0 | 100.0 | 100.0 |
| Adhesion ratio (%) | 74 | 75 | 63 | 64 |
| Spattering of powder | ⊚ | ⊚ | ○ | ○ |
| Excessive cold feel/pain | ⊚ | ⊚ | xx | xx |

Specifications of valve: stem orifice 0.51 mm×2, housing orifice 1.58 mm and vapor tap orifice 0.76 mm. Orifice of button: 1.02 mm.

In Examples 8 and 9, the powders little spattered, high adhesion ratios were achieved and no excessive cold feel or pain was observed, as Table 3 shows. Although the powders little spattered and high adhesion ratios were observed in Comparative Examples 6 and 7, these samples were not favorable in giving excessive cold feel and pain.

INDUSTRIAL APPLICABILITY

The powdery aerosol preparations according to the invention show largely improved adhesion to the skin and regulated spattering of drugs, which minimizes the fear of inhalation from the viewpoint of safety. Moreover, these preparations give no pain at the spraying and can be dried quickly, thereby imparting an excellent feel in using.

What is claimed is:

1. A powdery aerosol preparation for adhering to the skin by topical application comprising:
    (a) 50 to 90% by weight of a propellant, having a vapor pressure at 20° C. of 4.5 kg/cm² or less, selected from the group consisting of propane, n-butane, isobutane, dimethyl ether and mixtures thereof,
    (b) 5 to 30% by weight of an aliphatic hydrocarbon selected from the group consisting of n-pentane, isopentane, neopentane and mixtures thereof, and
    (c) 0.5 to 20% by weight of a powdery cosmetic or pharmaceutical component suitable for topical application to the skin, said preparation being packed in a container provided with a straight nozzle having an orifice of 0.7 to 2.0 mm.

2. The powdery aerosol preparation as claimed in claim 1, which contains 1–20% by weight of a lower alcohol selected from the group consisting of ethanol, isopropyl alcohol and a mixture thereof.

* * * * *